United States Patent [19]

Fruehwirth

[11] Patent Number: Plant 7,710

[45] Date of Patent: Nov. 12, 1991

[54] POINSETTIA PLANT '268 PINK'

[75] Inventor: Franz Fruehwirth, Encinitas, Calif.

[73] Assignee: Paul Ecke Ranch, Inc., Encinitas, Calif.

[21] Appl. No.: 528,232

[22] Filed: May 24, 1990

[51] Int. Cl.[5] ..... A01H 5/00

[52] U.S. Cl. ..... Plt./86

[58] Field of Search ..... Plt./86, 86.1, 86.3

*Primary Examiner*—Howard J. Locker

*Attorney, Agent, or Firm*—Arnold, White & Durkee

[57] ABSTRACT

Poinsettia cultivar '268 Pink' is a sport of cultivar '268' (U.S. Ser. No. 07/263,155) with large, bright pink erect flower bracts. '268 Pink' like its parent '268' is unique because the flower bracts remain erect and do not droop even after commercial shipping and handling or as the flowers mature. It always looks "fresh" which adds to its beauty and increases its value as a consumer product. Poinsettia '268 Pink' has the same flowering response time and cultural requirements as its parent '268'.

1 Drawing Sheet

BACKGROUND OF THE NEW PLANT

This new Poinsettia cultivar originated as a color sport of '268' (U.S. Plant Pat. No. 7,275) in a greenhouse in Encinitas, Calif. It was selected from many plants because of its early large, erect and bright pink flower bracts and self-branching traits which distinguish it from other poinsettia cultivars and seem to make it a desirable plant for commercial greenhouse production. After selection, stem cuttings of this plant were vegetatively reproduced for test purposes in Encinitas, Calif., and clones of this plant were subjected to successive generations of vegetative propagation which demonstrated that its distinctive characteristics hold true from generation to generation.

DESCRIPTION OF THE PHOTOGRAPHS

Poinsettia '268 Pink' is illustrated in the accompanying color photographs. The upper photo is a side view of three unpinched '268 Pink' plants, in a 14 cm. pot. The lower photo is a top view of the '268 Pink' plants showing flower and bract formation.

DESCRIPTION OF THE PLANT

The following is a detailed description of this new Poinsettia as observed in my greenhouse in Encinitas, Calif., during Dec. 1989. Observations were recorded from flowering plants, grown as 3 unpinched plants per pot. The pot was 14 cm. in diameter and 11 cm. in height. Color designations were compared to the 1986 edition of R.H.S. Colour Chart, first published in 1966 by the Royal Horticultural Society, London, England.

The Plant

Origin: Sport of '268' (U.S. Ser. No. 07/263,155).

Classification:

*Botanic.*—*Euphorbia pulcherrima* Willd.

*Common name.*—Poinsettia.

*Cultivar name.*—'268 Pink'.

Form: Shrub.

Height: Short.

Growth habit: As a single stemmed plant, upright and vigorous with several self-branching axillary stems. The application of a chemical growth retardant may not be needed to restrict height for commercial pot plant production. I observed 3 plants in a pot with an overall height of 42 cm. and an overall width of 45 cm. The bract diameter of individual flowers was 30 cm.

Branching: Poinsettia '268 Pink' like its parent plant '268' has self-branching traits. Branching can be enhanced by removal of the stem tip. Then, several flowering branches with equal vigor will develop on a single plant.

Growth rate: Very fast. Rooting of stem cuttings occurs in 12–18 days under intermittent mist. The plant will flower in about nine weeks under continuous long night conditions and night temperatures of about 16–18 degrees C.

Foliage: The foliage is clean and uniformly green from bottom to top of the plant. The leaves are of medium size, leaf blades typically being about 11–13 cm. long and about 9–10 cm. wide with leaf petioles about 5–6 cm. long.

*Leaf shape.*—Typical leaves are ovate with obtuse bases and acuminate tips. Leaf margins are mostly lobed with 2 indentations on each side of the leaf blade.

*Color.*—Upper side—Green, near R.H.S. 137A. Under side—Between R.H.S. 147B and R.H.S. 147C.

*Retention.*—*The foliage lasts fairly well even under low light intensities in the consumer's home.*

Bracts: Generally there are 18–24 uniformly colored bracts of various sizes subtending the cyathia. The primary bracts have blades typically 13–15 cm. long and 9–11 cm. wide with petioles about 3–4 cm. long. Bract attitude is similar for both '268 Pink' and its parent '268'.

*Shape.*—*Bracts are mostly ovate with acute bases and acuminate tips. Primary bracts are lobed with two indentations on either side of the bract. Secondary bracts have entire margins.*

*Color.*—Upper side—Bright pink, near 51C. Under side—Pink, brighter than R.H.S. 54C, near R.H.S. 55B.

Flowers: Generally, 12–15 cyathia (flowers) are present when the plant is in full bloom. Each cyathium is about 8 mm long and about 5 mm wide, light green in color and fringed with dark pink at the distal end. One yellow nectar cup protrudes from the side of each cyathium. The flower pedicel is also light green and about 5–6 mm in length. The stamens protruding from the cyathia are pink.

What is claimed is:

1. A new and distinct Poinsettia cultivar, substantially as herein shown and described, characterized by its early large, erect and bright pink flower bracts and self-branching traits.

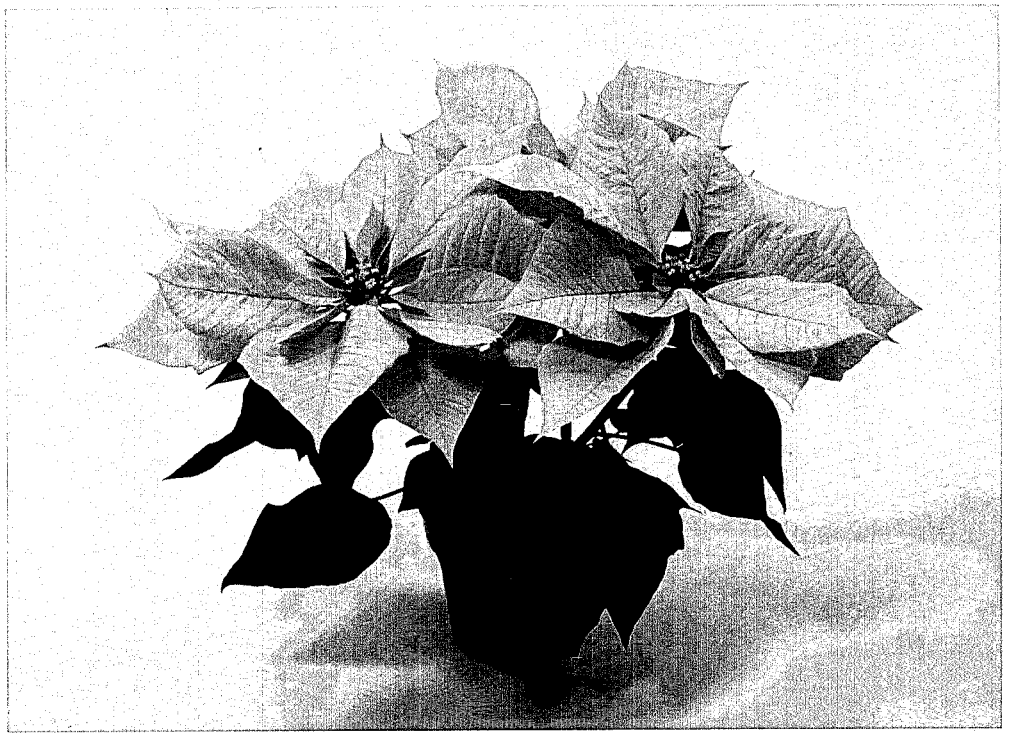
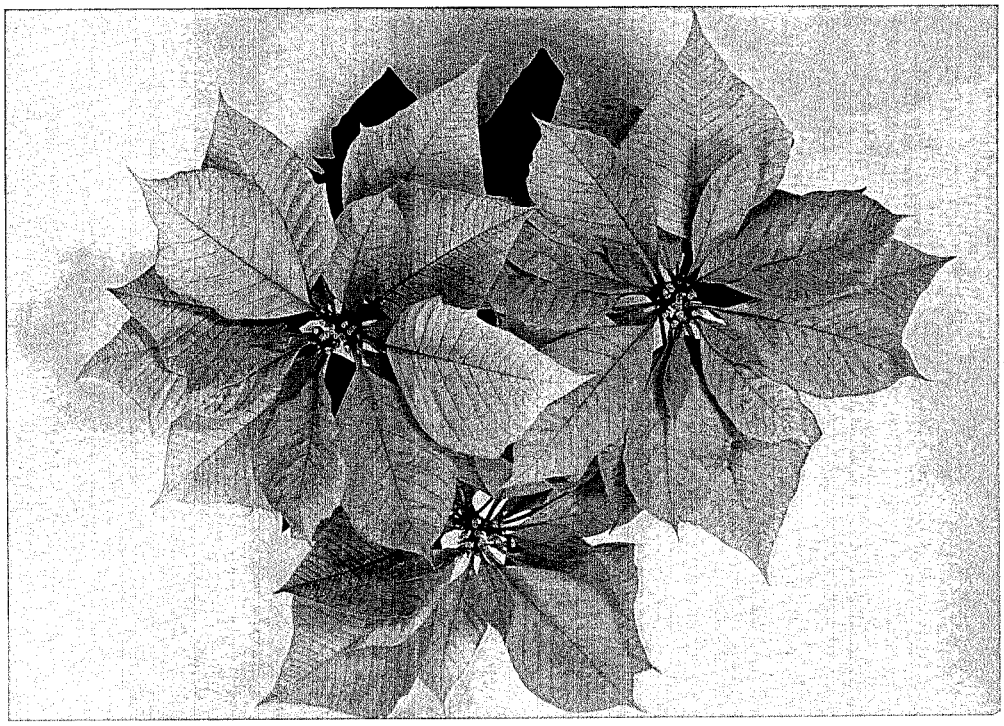

* * * * *